US010094900B2

(12) United States Patent
Greiser

(10) Patent No.: US 10,094,900 B2
(45) Date of Patent: Oct. 9, 2018

(54) 4D VELOCITY PROFILE IMAGE RECORDING WITH A MAGNETIC RESONANCE SYSTEM

(71) Applicant: Siemens Aktiengesellschaft, Munich (DE)

(72) Inventor: Andreas Greiser, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 767 days.

(21) Appl. No.: 14/719,657

(22) Filed: May 22, 2015

(65) Prior Publication Data

US 2015/0338490 A1 Nov. 26, 2015

(30) Foreign Application Priority Data

May 22, 2014 (DE) .................... 10 2014 209 803

(51) Int. Cl.
| | |
|---|---|
| *G01R 33/563* | (2006.01) |
| *G01R 33/385* | (2006.01) |
| *G01R 33/56* | (2006.01) |
| *G01R 33/30* | (2006.01) |
| *G01R 33/567* | (2006.01) |

(Continued)

(52) U.S. Cl.
CPC ..... *G01R 33/56316* (2013.01); *G01R 33/307* (2013.01); *G01R 33/385* (2013.01); *G01R 33/5608* (2013.01); *G01R 33/5673* (2013.01); *G01R 33/56375* (2013.01); *A61B 5/055* (2013.01); *G01R 33/56383* (2013.01); *G01R 33/56518* (2013.01); *G01R 33/56572* (2013.01); *G01R 33/56581* (2013.01)

(58) Field of Classification Search
CPC ............ G01R 33/56316; G01R 33/385; G01R 33/5608; G01R 33/307; G01R 33/56375; G01R 33/5673; G01R 33/56383; G01R 33/56518; G01R 33/56572; G01R 33/56581; A61B 5/055
See application file for complete search history.

(56) References Cited

U.S. PATENT DOCUMENTS

| | | | |
|---|---|---|---|
| 4,720,679 A | * | 1/1988 | Patrick .................. G01R 33/24 324/309 |
| 5,195,525 A | | 3/1993 | Pelc |
| 6,031,374 A | | 2/2000 | Epstein et al. |

(Continued)

OTHER PUBLICATIONS

Greiser et al., "Application of Highly Accelerated Cartesian Phase Contrast Imaging Using Compressed Sensing and Iterative Reconstruction to Real-Time and Vector Encoded Flow Imaging," Siemens Healthcare Pub. 7473 (2013).

*Primary Examiner* — Dixomara Vargas
(74) *Attorney, Agent, or Firm* — Schiff Hardin LLP

(57) ABSTRACT

In a method and device for generating 4D flow images by operation of a magnetic resonance system, a volume flow data record is recorded, wherein the flow is encoded in a single direction. This is subsequently repeated with all the flow encoding directions. From the raw data associated with the individual flow encoding directions, phase images and magnitude images are calculated. Deformation fields are calculated on the basis of the magnitude images. The deformation fields are applied to the calculated phase images. Finally, a 4D flow velocity field is calculated, on the basis of a phase difference reconstruction of the corrected phase images.

14 Claims, 2 Drawing Sheets

(51) Int. Cl.
 *A61B 5/055* (2006.01)
 *G01R 33/565* (2006.01)

(56) References Cited

U.S. PATENT DOCUMENTS

| | | | | |
|---|---|---|---|---|
| 6,892,089 | B1 * | 5/2005 | Prince | A61B 5/055 128/922 |
| 8,085,041 | B2 * | 12/2011 | Aksit | G01R 33/243 324/307 |
| 9,008,399 | B2 * | 4/2015 | Fain | G01R 33/5601 382/131 |
| 2003/0135103 | A1 | 7/2003 | Mistretta | |
| 2011/0153231 | A1 | 6/2011 | Greiser et al. | |
| 2014/0212012 | A1 * | 7/2014 | Fain | G01R 33/5601 382/131 |
| 2016/0213341 | A1 * | 7/2016 | Salcudean | A61B 6/50 |

\* cited by examiner

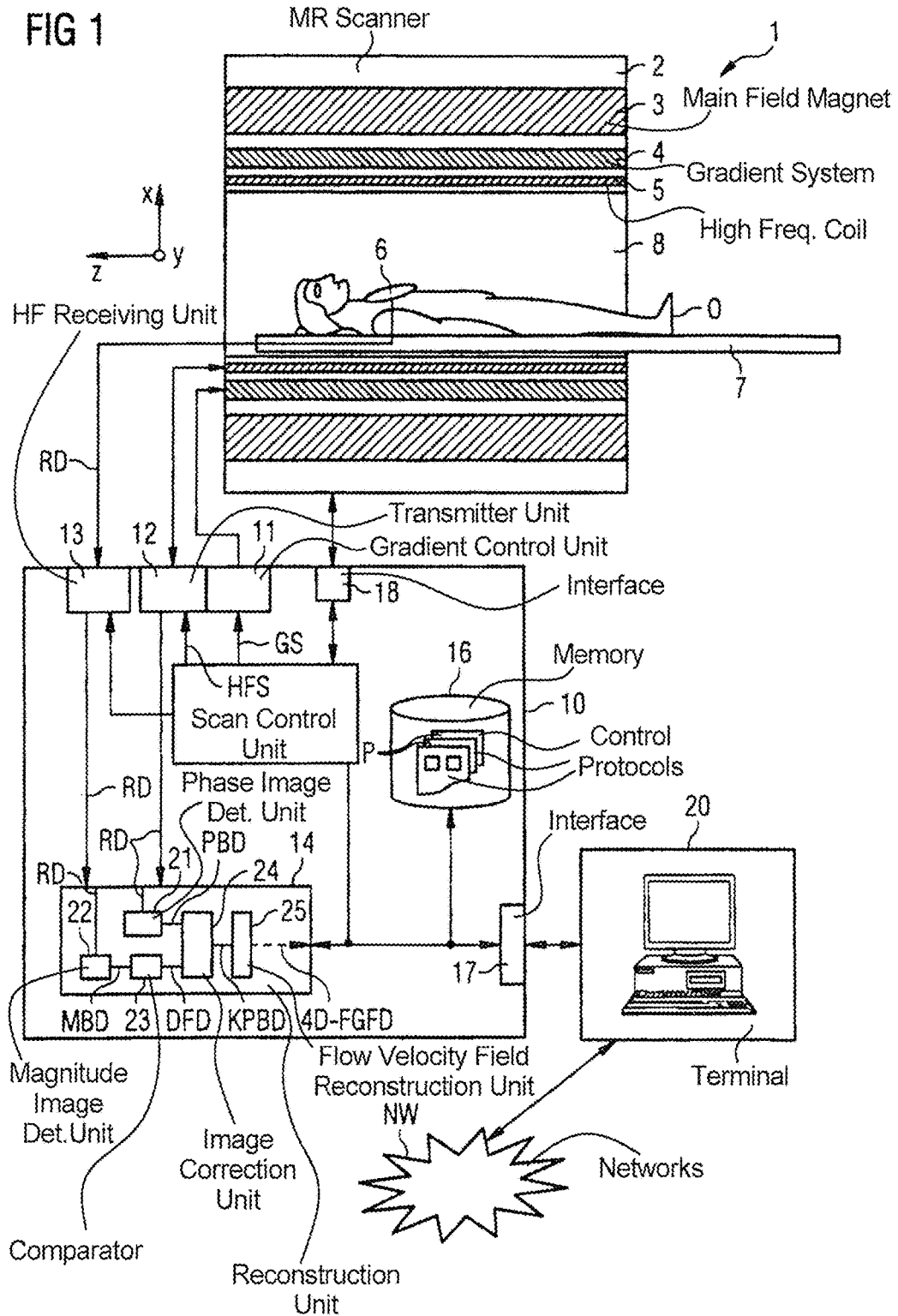

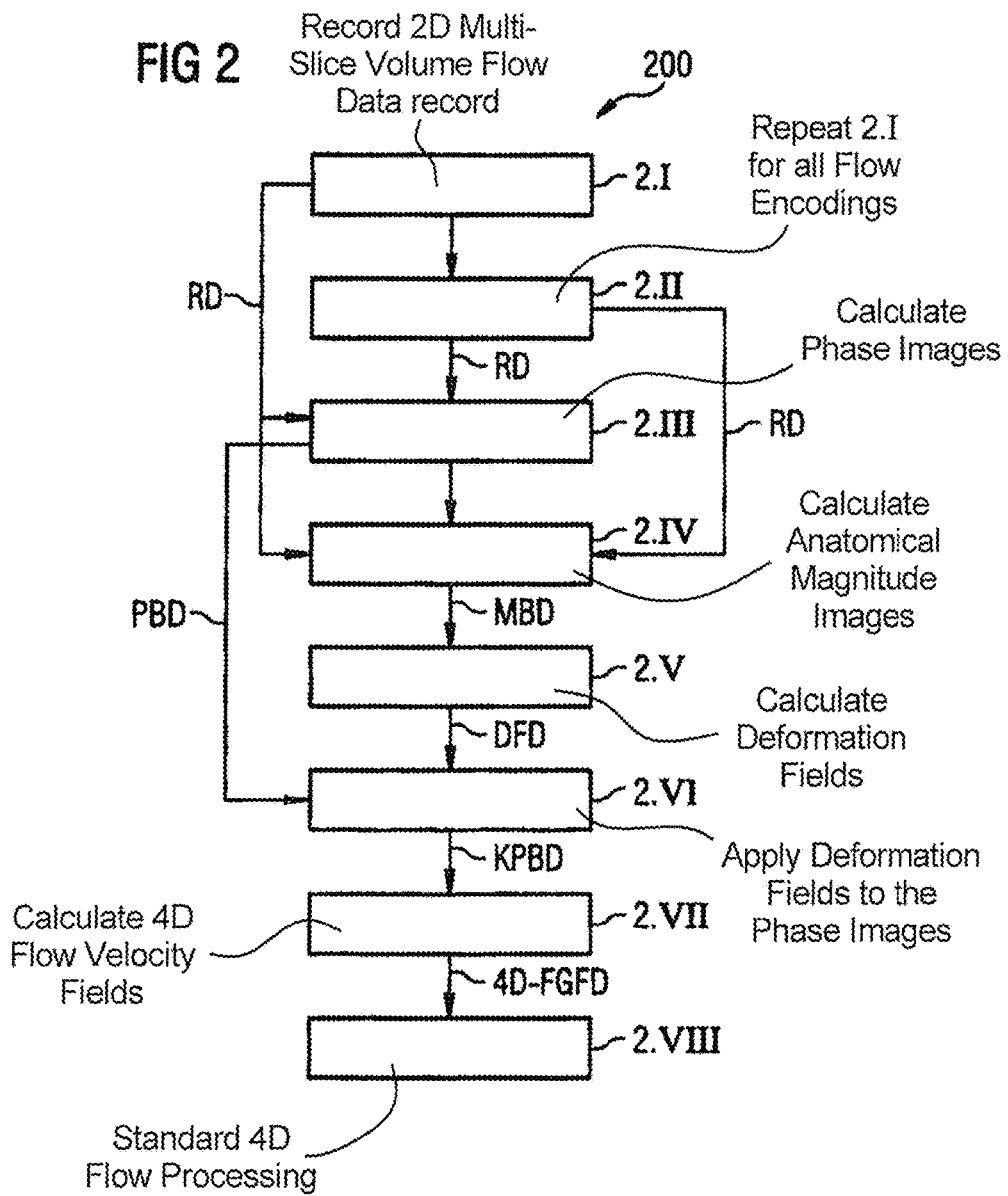

4D VELOCITY PROFILE IMAGE RECORDING WITH A MAGNETIC RESONANCE SYSTEM

BACKGROUND OF THE INVENTION

Field of the Invention

The invention concerns a method for generating 4D flow images by operation of a magnetic resonance system and a device for generating 4D flow images by operation of a magnetic resonance system. The invention also concerns such a magnetic resonance system.

Description of the Prior Art

MR phase contrast flow imaging (also known as "phase contrast flow imaging") is a non-invasive quantitative method which is usable in vivo. Phase contrast flow imaging is based on the different phases that can develop during an MR recording under transverse magnetization. In the presence of time-varied gradient fields, a moving magnetization in the outer B0 field accumulates one phase. This can be used to encode velocities. For this purpose, the different influences of the MR imaging on the magnetization is compensated for by special gradient switching sequences such that only phase differences which form due to the movement of the magnetization remain, for example, during the flow of blood in a vessel relative to the stationary vessel wall. Otherwise expressed, due to the application of a bipolar gradient, the magnetization of the flowing material attains a phase offset which is proportional to the velocity of the flowing particles. Static examination regions ideally do not have this phase. The phase information of an MR signal is contained in the imaginary portion of the signal which, in conventional MR scans is typically discarded or is set against the actual anatomical magnitude image. In the normal case, the imaginary portion of the signal does not contain any meaningfully useful information. However, during a phase contrast scan, the imaginary portion is reconstructed, as a separate data record, into a phase image. This phase image contains encoded in each image point as a gray scale value the information concerning the velocity and direction of the corresponding image point or image voxel. The direction is encoded as a gray scale. At white image points, the flow is directed toward the observer and at black image points, the flow is directed away from the observer.

In the phase contrast flow scan, different interference phenomena which can impair the result arise. One phenomenon is "phase wrap-around" or the aliasing that is attributable thereto. This is based on the fact that only values of the phase of the transverse magnetization from the +180° to the −180° directions are correctly recognized. All values beyond this are not correctly recognized and are erroneously represented as flows with the opposite direction in the data record or in the phase image. Therefore, before a phase contrast scan, the velocity range of the region to be investigated or of the fluids moving therein must be specified. The gradient profile of the sequence is modified such that the maximum phase difference of +−180° corresponds to the velocity range given. This velocity is denoted "encoding velocity" (VENC). Values of VENC that are too low lead to the aforementioned aliasing. Conversely, the noise of phase contrast flow imaging increases with the height of the VENC so that with the VENC selected to be too high, falsification of the measurement results can also be expected.

Further errors arise from phenomena which occur due to eddy currents and Maxwell terms (magnetic fields of high order). For this reason, in a phase contrast flow imaging scan, the phase of the static regions is also not exactly zero. In order to compensate for the aforementioned errors, the Maxwell terms can be calculated and the images can be corrected with the computation results. However, the eddy currents are much more difficult to correct or compensate for, since they are very difficult to predict.

Recently, a new type of phase contrast imaging called "4D flow" has been developed with which a complete vectorial measurement of flow fields in one volume can be achieved. Herein, velocity information over time is generated in a three-dimensional space. The recording time of a 4D flow data record is typically very long due to the multiple velocity encodings in different directions and a spatial and temporal coverage of the region to be investigated or the required spatial or temporal resolution associated therewith. Furthermore, a navigator is typically used in order to enable clocking of the recording with the breathing rhythm during a long-duration recording time. In this way, recording times of approximately 15 minutes are achieved.

Compared with the established phase contrast flow imaging for the measurement of the flow velocities, wherein a single slice is recorded with a flow encoding perpendicular to the slice plane, in the "4D flow" sequence, data are recorded with a plurality of flow encoding directions (flow-compensated (resultant first magnetic moment M1=0), vx, vy, vz). Typically, the innermost loop in the sequence is designed such that data for a number of different flow encoding directions can be recorded therein. For recording the vector field, bipolar gradients are applied. Since the bipolar gradients for different flow encoding directions are applied in different directions, the effectively repeated gradient pattern which gives rise to the eddy currents in the stationary state is repeated during the recording of a 4D flow protocol in a time interval which corresponds to the effective repetition time TR(4D)=4×ES, wherein ES describes the echo spacing of the underlying imaging sequence, which repeats according to the number of velocity encoding directions as compared with simple phase contrast flow imaging. For this reason, the eddy currents arising in equilibrium (after many repetitions of the gradient pattern) are possibly stronger and the background phase connected thereto with "4D flow" is higher than with flow encoder protocols with a single velocity direction where the same velocity encoding gradient is applied at the time offset of a shorter repetition time TR(2D)=2×ES.

Furthermore, there are measures with which a more rapid image recording is ensured wherein the overall recording time can be achieved in the order of a few minutes, making use of a classic navigator.

Furthermore, improved movement registration techniques are also available, permitting registration of data records over a plurality of breathing cycles. The acceleration of the 4D flow technology to a duration of a few breaths would enable a clinical application.

However, the conventional procedure for 4D flow image recordings results in the following difficulties. Conventionally, for 4D flow image recording, the velocity encoding is carried out in the innermost loop, while the patient table is stationary. Due to the rapid gradient changes, eddy currents are formed, resulting in a background signal which intensifies with distance from the isocenter.

Furthermore, the following problems exist, which make a clinical application of the 4D flow method more difficult. Firstly, the recording times for "4D flow" are still too long and, secondly, more intense eddy currents occur, particularly with an accelerated procedure, due to the more complex flow encoding scheme and the different flow encoding directions for "4D flow".

SUMMARY OF THE INVENTION

An object of the present invention is to develop a more rapid, more precise and less fault-prone method for generating 4D flow images.

In the method for generating 4D flow images according to the invention, initially a volume flow data record is recorded (acquired) wherein the flow is encoded in a single direction. The previous step is repeated with one flow encoding direction, preferably multiple flow encoding directions, particularly preferably all the other flow encoding directions. From the data recorded and associated with the respective flow encoding directions, phase images are calculated. Furthermore, anatomical magnitude images are calculated from all the flow encoding directions or velocity encodings. Then, on the basis of the magnitude images, deformation fields are calculated and the resulting deformation fields are applied to the corresponding phase images which result from the respective data associated with the velocity encodings. By applying the deformation fields to the phase images, the distortions which result from the temporal offset with which the data associated with the different encoding directions are recorded are corrected. Finally, a 4D flow velocity field based on a phase difference reconstruction of the corrected phase images is calculated. With the above-mentioned method, a shortening of the recording time and an improved image quality are achieved on the basis of the lessening of eddy currents.

A basis of the method according to the invention is the implementation of a sequential recording of the raw data associated with the individual flow encoding directions. Despite the individual flow encoding direction stipulated for a given volume or for a slice or a slice package for a specified recording time point or a recording time interval, the velocities associated with the different encoding directions can be determined or reconstructed for a specified time point. This is achieved on the basis of magnitude images determined from data recorded at different time points or from the deformation fields to be determined therefrom, which result from the temporal change in the examination object or through the temporal offset of the recording of the data associated with the individual magnitude images. Thus, despite the sequential recording of the data associated with the individual flow encoding directions, determination of a three-dimensional velocity field is made possible. In contrast to the conventional method, during the scanning of a region under investigation, the encoding direction is only changed after a complete scan, for example, in the case of a slice-selective scan of a slice or of a slice package consisting of a plurality of slices, which corresponds to the recording of a 2D multiple-slice volume flow data record. The encoding direction or the flow encoding direction is given by the direction in which the bipolar gradient fields are applied. On the basis of the change in the flow encoding direction only after scanning a complete slice or a complete slice package, the rate of change of the gradient pulses is reduced and thus the artifacts described above are reduced.

From the raw data, both phase images and also anatomical magnitude images can be calculated. From the magnitude images, deformation fields can be calculated which are applied to the phase images which result from the data associated with the respective flow encoding directions. If an individual encoding block is too time-consuming, a subset of each block can be recorded in a movement cycle of the examination object, for example a breath, and the data for a plurality of breaths can be corrected with regard to the movements. Rather than reducing the sampling time, the temporal resolution can also be increased. For example, all encodings can be recorded effectively at the same time points within a movement cycle of a target object and the data for the different velocity directions can be recorded sequentially. In particular, the movement cycle can be a heartbeat cycle or a breathing cycle.

The device according to the invention for creating 4D flow images by means of a magnetic resonance system has a control unit which is configured to generate a pulse sequence for a phase contrast measurement in order to record a volume flow data record. The control unit can be, for example, a suitably programmed scan control computer of a magnetic resonance system. Firstly, the flow is encoded for a slice or a slice package or a volume region in just one single direction. Subsequently, the recording is repeated for this slice or the slice package or alternatively for the volume region in all the flow encoding directions. The device has a phase image determination unit which is configured to calculate phase images from the data which are associated with the respective flow encoding directions. Furthermore, the device has a magnitude image determination unit which is configured to calculate anatomical magnitude images from the data which are associated with the respective flow encoding directions. More precisely expressed, the data recorded for the phase contrast measurement are additionally used to generate magnitude images, from the change or deformation of which conclusions can be drawn about the changes which have occurred between the recordings with different velocity encodings. Additionally, the device has a comparator unit which is configured to calculate deformation fields on the basis of the magnitude images. The deformation fields provide information on the change in the object to be investigated which occurs between the individual encoding time points. Additionally, the device has a phase image correction unit which is configured, on the basis of the deformation fields resulting from the magnitude images, to correct the calculated phase images. Finally, the device has a 4D flow velocity field reconstruction unit which is configured to reconstruct a 4D flow velocity field on the basis of a phase difference reconstruction of the corrected phase images.

The magnetic resonance system according to the invention has such a device according to the invention.

The invention also encompasses a non-transitory, computer-readable data storage medium that can be loaded directly into a memory of the device according to the invention, with program code in order to carry out all the steps of the method according to the invention when the code is executed in the device according to the invention. Such a software-based realization has the advantage that conventional control devices of magnetic resonance systems can be modified by implementing the program in a suitable manner in order to specify a scan protocol in the manner according to the invention, the protocol being associated with the aforementioned advantages, for example.

According to a preferred embodiment of the method according to the invention, the volume flow data record comprises a 2D multiple-slice volume flow data record or alternatively a 3D volume flow data record. In the case of the 2D volume flow data record, initially a complete scan is carried out in a single encoding direction or flow encoding direction for a slice or a slice package. Only thereafter is the encoding direction changed and the scan of said slice or slice package is repeated with the changed encoding direction. On the basis of the change in the flow encoding direction only after scanning a complete slice or a complete slice package, the rate of change of the gradient pulses is reduced.

According to an alternative embodiment of the method according to the invention, in place of the 2D multiple-slice volume flow data record, a 3D volume flow data record is recorded. In this case, therefore, no individual slices are recorded one after the other, but rather three-dimensional regions are scanned one after the other in different encoding directions.

According to a preferred embodiment of the method according to the invention, the volume flow data record is recorded during a single movement time segment or movement cycle of the examination object, for example, during a single breath. More precisely expressed, a data record is advantageously recorded during the interval between two breathing time points. The data record with the next encoding direction can then be recorded in the next interval between two breathing time points. By this procedure, the artifacts generated by the breathing movement do not arise as they do in conventional methods.

In order to accelerate the image recording, the volume flow data record can be recorded on the basis of an accelerated method such as PAT or incoherent undersampling (compressed sensing). In this regard, undersampling is deliberately undertaken for the individual encoding directions and the missing data are reconstructed by more complex iterative methods.

The method according to the invention can also be modified or enhanced by recording the volume flow data record with a movement of the examination object during the scan, in order to restrict the recording to the region close to the isocenter. For example, the method according to the invention can be configured as a recording method with a moving patient table ("Tim-CT"). This recording method is typically carried out with an axial single-exposure module, while the table is continuously moved. The restriction of the recording region to the isocenter makes it possible that on 4D flow scans, the eddy currents, the non-linear gradients and the possible Maxwell errors are reduced, since all the slices are recorded close to the isocenter where these effects are minimized.

By contrast, during a 4D flow recording with a fixed table position, negative effects are noticeable due to the contributions of eccentric positions. At a distance from the isocenter of from several centimeters up to half the FOV (field of view) in the z-direction of the MR system, the deviations can easily reach the order of magnitude of a few percent of the measured velocity, which represents a significant problem for the accuracy of such flow imaging processes.

According to one embodiment, in the method according to the invention, the step of the sequential flow image recording with all the flow encoding directions can be carried out flow-compensated and/or in a vx-direction, a vy-direction, a vz-direction and/or with another encoding scheme. Furthermore, as an encoding scheme, for example, a tetrahedral or any other desired scheme can be used.

In a particularly preferred variant of the method according to the invention, in accordance with the method steps described, i.e. after calculating a 4D flow velocity field, a standard 4D flow processing scheme is applied for analysis and imaging, in order to realize imaging of the acquired data. Therefore, already existing image processing methods can also be used subsequently to the steps of the method according to the invention in order to enable or to improve imaging of the phase-contrast scan.

Since a single velocity encoding recording can be carried out with a high temporal resolution, for example, at a frame rate of 40 ms, in the 4D flow image recording method according to the invention, the movement artifacts, for example, in the case of the recording of 2D multiple-slice volume flow data records, are minimal over the successively recorded slices and the movement due to a moving object under investigation, for example, the heart contraction and/or the breathing movement, can be resolved in the acquired image series. Therefore, the typical zigzag artifacts, as are known in the method for recording a single image per heart movement (for example, in QISS) are not to be expected.

If the reduction of eddy currents in successive scans is not relevant for different flow encodings, it may nevertheless be advantageous to use this scanning method with a moving patient table with a plurality of different encodings, since the individual encoding data records which were recorded in real time cover the continuous movement of the examination region and therefore the registration should be better than in an overlapped recording in which the different encodings are recorded in the innermost loop, so that in the conventional approach, a loss of temporal resolution by a factor of the total count of the encodings or encoding directions must be accepted.

In order to take into account physiological changes over different encoding episodes, the data for a changing heart frequency can be corrected by means of interpolation or extrapolation algorithms, which can be applied in a similar way as in a triggered retrogating reconstruction. In this regard, the data measured during one heartbeat in a particular k-space segment are interpolated to a mean RR interval before the reconstruction of all k-space data is carried out.

The effect of the movement of the examination object on the flow-sensitive signal recording due to the table movement during a recording of a single slice or of a single slice package can be prevented, for example, in the case of the recording of 2D multiple-slice volume flow data records by compensation of the continuous table movement by displacing the scan slice relative to an isocenter of the magnetic resonance system used in the direction opposite to the table movement. At the start of the recording of the next slice, the slice position is then displaced due to the table movement to the next position to be recorded within the patient, whilst a slice movement during the recording of the individual slides or the slice package can be prevented. Thus the slice moves until a slice is finished and then jumps to the next slice position in the patient, which then moves on with the continuously displaced patient, and so on.

The table speed can be adapted to the changes in the physiological parameters, such as the heart rate or the breathing rate. Due to the use of Tim-CT in conjunction with the vector-encoded phase-contrast recording, the usable z-FOV, i.e. the image region in the z-direction, can be extended to regions typically reached with the Tim-CT method of up to 200 cm without the above-mentioned problems, such as the occurrence of eddy current effects and non-linear gradients. The combination of the constant displacement of the table and the above-mentioned recording methods enable a yet better minimization of eddy currents which are generated in the conventional method due to the rapid change in the velocity encoding direction in the innermost loop of the recording sequence. The above-mentioned method can also be realized as an undersampled method. The recording in real time can be realized in a classic manner wherein a separate reference recording with flow compensation is made for each velocity encoding direction. The recording with flow compensation has the advantage that the compensated and the encoded scan fit together better due to the temporal proximity.

Alternatively, in order to increase the recording speed, a true single flow encoding can be recorded with each movement, i.e. the first movement with flow compensation, the second with vx-encoding, the third with vy-encoding and the fourth with vz-encoding. This type of method would imply an additional velocity increase by 50% (4 rather than 3 times 2 recordings).

By means of the sequential recording of the 4D flow data for different velocity encodings, real time data recording is made possible and sufficient spatial coverage is achieved in a short time period (in one breath for the greatest acceleration of the recording). Furthermore, a reduction in the eddy currents is achieved as a result of the VENC switch-over by means of the described sequential recording of the raw data for the individual velocity encodings. In this process, simultaneous recording of magnitude images for each velocity encoding and the application of the deformation fields to the phase images prevents a worsening of the quality of the recording due to the distortions caused by the temporal offset of the recording. If this recording technique is combined with a recording with a moving table, effects such as, for example, eddy currents, non-linear gradients and residual Maxwell effects, such as occur in a decentered recording of phase-encoded images can also be minimized.

As described above, an additional correction as compensation for the moving table is achieved in that the scan slices are moved in the direction opposite to the movement direction of the table. By recording with a moving table, an extended spatial coverage is also achieved. An additional increase in the velocity of the recording is enabled with the method according to the invention since clocking with a navigator can be omitted.

BRIEF DESCRIPTION OF THE DRAWINGS

FIG. 1 schematically illustrates a magnetic resonance system according to an exemplary embodiment of the invention.

FIG. 2 schematically illustrates the method of the invention according to an exemplary embodiment.

DESCRIPTION OF THE PREFERRED EMBODIMENTS

Shown in FIG. 1 in schematic form is a magnetic resonance system 1 configured according to the invention. The system 1 includes the actual magnetic scanner 2 with an examination space 8 or patient tunnel 8 situated therein. A table 7 can be moved into this patient tunnel 8 so that a patient O or test subject lying thereon can be placed during an examination at a particular position within the magnetic resonance scanner 2 relative to the magnetic system and the high frequency system arranged therein and is also displaceable during a scan between different positions.

Basic components of the magnetic resonance scanner 2 are a main field magnet 3, a gradient system 4 with magnetic field gradient coils for generating magnetic field gradients in the x, y and z directions and a whole body high frequency coil 5. The magnetic field gradient coils are controllable independently of one another in the x-, y- and z-directions, so that by means of a pre-set combination, gradients can be applied in any desired logical spatial directions (for example, in the slice selection direction, in the phase-encoding direction or in the readout direction), wherein these directions typically depend on the selected slice orientation. Equally, the logical spatial directions can also match the x-, y- and z-directions, for example, the slice selection direction in the z-direction, the phase encoding direction in the y-direction and the readout direction in the x-direction. The reception of magnetic resonance signals induced in the examination object O can take place with the whole body coil 5, with which typically the high frequency signals for inducing the magnetic resonance signal are also emitted. Usually, however, these signals are received with a local coil arrangement 6 with, for example, local coils (of which only one is shown here) placed on or under the patient O. All these components are known, in principle, to those skilled in the art and are therefore shown only schematically in FIG. 1.

The components of the magnetic resonance scanner 2 are controllable by a control device 10. This can be a control computer composed of multiple individual computers, possibly spatially separated and connected to one another by means of suitable cables or the like. This control device 10 is connected, by a terminal interface 17, to a terminal 20, via which an operator can control the entire system 1. In the present case, this terminal 20 is equipped as a computer with a keyboard, one or more screens and further input devices such as a mouse or the like, so that a graphical user interface is available to the user.

The control device 10 has, inter alia, a gradient control unit 11 which can itself consist of a plurality of component parts. By means of this gradient control unit 11, the individual gradient coils have control signals applied to them according to a gradient pulse sequence GS. This involves gradient pulses as described above which, during a scan, are placed (played out) at precisely pre-determined temporal positions and according to a precisely pre-determined temporal sequence.

The control device 10 also has a radio frequency transmitter unit 12 in order to feed high frequency pulses to the whole body radio frequency coil 5 according to a pre-determined radio frequency pulse sequence RFS of the pulse sequence. The radio frequency pulse sequence RFS includes, for example, excitation and refocusing pulses. The reception of the magnetic resonance signals then takes place with the use of the local coil arrangement 6 and the raw data RD received thereby are read out and processed by an HF receiving unit 13. The magnetic resonance signals are passed, in digital form, as raw data RD to a reconstruction unit 14, which reconstructs the image data BD therefrom and then places the image data in a memory 16 and/or passes the image data, via the interface 17, to the terminal 20 so that the user can view the image. The image data BD can also be stored and/or displayed and evaluated at other sites via a network NW. The image data BD include the classic image data reconstructed from the magnitude data of the raw data RD, as well as the phase images generated in the phase contrast scan from the imaginary parts of the raw data.

Alternatively, a radio frequency pulse sequence can be emitted via the local coil arrangement and/or the magnetic resonance signals can be received by the whole body radio frequency coil (not shown), depending on the current connection of the whole body radio frequency coil 5 and of the coil arrangements 6 to the radio frequency transmitting unit 12 or the RF receiving unit 13.

Via a further interface 18, control commands are transferred to other components of the magnetic resonance scanner 2, for example, the table 7 or the main field magnet 3, or measurement values or other information are accepted.

The gradient control unit 11, the RF transmitting unit 12 and the RF receiving unit 13 are each coordinated by a scan control unit 15. The scan control unit ensures, with relevant commands, that the desired gradient pulse sequences GS and the radio frequency pulse sequences RFS are emitted. Furthermore, it must be ensured that, at the relevant time point, the magnetic resonance signals are read out to the local coils of the local coil arrangement 6 by the RF receiving unit 13 and are further processed. The scan control unit 15 also controls the further interface 18. The scan control unit 15 can be formed, for example, from a processor or multiple co-operating processors.

The underlying sequence of a magnetic resonance scan of this type and the above-mentioned components for control are known to those skilled in the art, so that they need not be discussed in further detail herein. Furthermore, a magnetic resonance scanner 2 of this type and the associated control device can also have a number of further components that also need not be discussed in detail herein. It should be noted that the magnetic resonance scanner 2 can be constructed differently, for example, with a laterally open patient space or as a smaller scanner in which only one body part can be positioned.

In order to start a scan, via the terminal 30, an operator can usually select a control protocol P which is provided for this measurement from a memory store 16 in which a plurality of control protocols P for different scans are stored. Furthermore, the operator can also call up control protocols via a network NW, for example, from a manufacturer of the magnetic resonance system and then, where relevant, modify and use them.

The scan control unit 15 is configured to generate 4D flow images. Put more precisely, the scan control unit 15 is configured to generate a pulse sequence for a phase contrast measurement in order to acquire a volume flow data record RD wherein the flow is encoded in a single direction and the recording is to be repeated in a plurality of flow encoding directions. For this purpose, the pulse sequence comprises, in particular, specific gradient pulses for bipolar gradient fields with which the velocity-dependent phase encodings of the spin are generated in a region to be investigated. The magnetic resonance system 1 also has a phase image determination unit 21. The phase image determination unit receives raw data RD from the receiving units 12 and/or 13 and calculates phase images PBD from the raw data RD or, more precisely, from the raw data associated with the respective flow encoding directions. The phase image determination unit is part of the reconstruction unit 14, in accordance with the exemplary embodiment shown in FIG. 1. In accordance with the exemplary embodiment shown in FIG. 1, the reconstruction unit 14 also comprises a magnitude image determination unit 22. The magnitude image determination unit 22 also receives raw data RD from the receiving units 12 and/or 13 and is configured to calculate anatomical magnitude images MBD for all velocity encodings, i.e. from the raw data RD which are associated with the respective flow encoding directions. The reconstruction unit 14 also has a comparator unit 23 that calculates deformation fields DFD on the basis of the anatomical images MBD. Otherwise expressed, from the magnitude images MBD associated with different time points, changes and/or the dynamics of the object being examined O are determined. The deformation field data DFD and the phase image data PBD are transferred to a phase image correction unit 24 which uses the deformation fields DFD resulting from the magnitude images on the relevant phase images PBD. In this way, the distortions of the phase images resulting from the temporal offset of the recording of the data underlying the phase images are corrected. The corrected phase images KPBD are transferred to a 4D flow velocity field reconstruction unit 25 which is configured to reconstruct a 4D flow velocity field 4D-FGFD on the basis of a phase difference reconstruction of the corrected phase images KPBD. The above-mentioned units can alternatively be realized as software, for example, on the terminal 20.

In FIG. 2, the method 200 according to a first exemplary embodiment is illustrated. In step 2.I, a 2D multiple-slice volume flow data record RD is recorded with a flow encoding in a single direction, preferably in a single breath. Herein, acceleration methods, for example, PAT, undersampling of split velocities (compressed sensing) can also be utilized, preferably in combination with a movement of the patient O during scanning, in order to restrict the recording to the region close to the isocenter. In step 2.II, the procedure in step 2.I is repeated for all the necessary flow encodings, for example flow-compensated, in the vx direction, the vy direction, in the vz direction or with other encoding schemes, for example, tetrahedrally. In step 2.III, phase images PBD are calculated from the data RD for the respective flow encoding directions. In step 2.IV, anatomical magnitude images MBD are calculated from the data RD for the respective velocity encodings or encoding directions. In step 2.V, deformation fields DFD are calculated on the basis of the magnitude images MBD. In step 2.VI, the deformation fields DFD are applied to the calculated phase images, i.e. the phase images PBD are corrected accordingly. In step 2.VII, 4D flow velocity fields are calculated on the basis of a phase difference reconstruction of the corrected phase images KPBD. In step 2.VIII, a standard 4D flow processing procedure is applied for analysis and visualization.

As mentioned above, this recording technique can be combined with a recording with a moving table, so that effects such as, for example, eddy currents, non-linear gradients and residual Maxwell effects, such as occur in a decentered recording of phase-encoded flow images can be minimized.

Finally, it should again be noted that the detailed methods and constructions mentioned above are exemplary embodiments and the basic principle can also be varied over a wide range by a person skilled in the art without departing from the field of the invention as defined by the claims. For completeness, it should be mentioned that the use of the indefinite article "a" or "an" does not preclude the relevant feature also from being present plurally. Similarly, the expression "unit" or "module" does not preclude that item from being formed by multiple components that may possibly also be spatially distributed.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for generating 4D flow images using acquired magnetic resonance (MR) data, comprising:
    operating an MR scanner to acquire a volume flow data record representing flow of a flowing medium in an examination subject situated in the MR scanner, including operating a gradient coil arrangement of the MR scanner to encode MR signals originating from said flow in a single flow encoding direction;
    operating said MR scanner to repeat acquiring said volume flow data record with said gradient coil arrangement being operated to encode said MR signals originating from said flow in a plurality of different flow encoding directions;

providing said volume flow data record, after repeating acquiring said volume flow data record, to a processor and, in said processor, reconstructing phase images from said volume flow data record, each phase image being respectively associated with a different flow encoding direction;

in said processor, reconstructing magnitude images from said volume flow data record, each of said magnitude images being respectively associated with a respective flow encoding direction;

in said processor, calculating deformation fields from said magnitude images;

in said processor, applying the calculated deformation fields to the reconstructed phase images, thereby obtaining a plurality of corrected phase images;

in said processor, calculating a 4D flow velocity field by executing a phase difference reconstruction algorithm using the corrected phase images; and making the calculated 4D flow velocity field available in electronic form at an output of said processor.

2. A method as claimed in claim 1 comprising operating said MR scanner to acquire said volume flow data record as a data record selected from the group consisting of a 2D multi-slice volume flow data record and a 3D volume flow data record.

3. A method as claimed in claim 1 comprising operating said MR scanner to acquire said volume flow data record during a single time segment of movement of the examination subject.

4. A method as claimed in claim 1 comprising operating said MR scanner with an accelerated data acquisition pulse sequence to acquire said volume flow data record.

5. A method as claimed in claim 1 comprising operating said MR scanner to acquire said volume flow data record during movement of the examination subject, and restricting acquisition of said volume flow data record to a region of the examination subject in proximity to an isocenter of said MR scanner.

6. A method as claimed in claim 5 comprising operating said MR scanner to acquire said volume flow data record from a plurality of slices of the examination subject and, from said control unit, operating said MR scanner to acquire said volume data flow record with movement that occurs during acquisition of signals representing said flow in a respective slice of the examination subject by extending the respective slice relative to the isocenter of the MR scanner.

7. A method as claimed in claim 1 wherein said repeating of acquiring said volume flow data record comprises repeating acquiring said volume flow data record for all flow encoding directions of a Cartesian coordinate system.

8. A method as claimed in claim 7 comprising operating said MR scanner to encode said MR signals originating from said flow according to a tetrahedral encoding.

9. A method as claimed in claim 1 comprising, in said processor, analyzing said flow represented in said 4D flow velocity field using a 4D flow processing algorithm to obtain a flow-analyzed 4D flow velocity field, and, from said processor, causing the flow-analyzed 4D flow velocity field to be displayed at a display screen in communication with said processor.

10. A method as claimed in claim 1 comprising operating said MR scanner to acquire said MR signals originating from said flow in said flow volume data record for all encoding directions at same points in time within a movement cycle of the examination subject, and acquiring said MR signals for respectively different flow encoding directions temporally offset by an echo time.

11. A method as claimed in claim 10 wherein said movement cycle is a cardiac cycle or a breathing cycle.

12. A device for generating 4D flow images using acquired magnetic resonance (MR) data, comprising:

a processor configured to operate an MR scanner to acquire a volume flow data record representing flow of a flowing medium in an examination subject situated in the MR scanner, including operating a gradient coil arrangement of the MR scanner to encode MR signals originating from said flow in a single flow encoding direction;

said processor being configured to operate said MR scanner to repeat acquiring said volume flow data record with said gradient coil arrangement being operated to encode said MR signals originating from said flow in a plurality of different flow encoding directions;

said processor being configured to, after repeating acquiring said volume flow data record, to reconstruct phase images from said volume flow data record, each phase image being respectively associated with a different flow encoding direction;

said processor being configured to reconstruct magnitude images from said volume flow data record, each of said magnitude images being respectively associated with a respective flow encoding direction;

said processor being configured to calculate deformation fields from said magnitude images;

said processor being configured to apply the calculated deformation fields to the reconstructed phase images, thereby obtaining a plurality of corrected phase images;

said processor being configured to calculate a 4D flow velocity field by executing a phase difference reconstruction algorithm using the corrected phase images; and said processor being configured to make the calculated 4D flow velocity field available in electronic form at an output of said processor.

13. A magnetic resonance (MR) apparatus comprising:
an MR scanner comprising a gradient coil arrangement;
a processor configured to operate said MR scanner to acquire a volume flow data record representing flow of a flowing medium in an examination subject situated in the MR scanner, including operating said gradient coil arrangement of the MR scanner to encode MR signals originating from said flow in a single flow encoding direction;

said processor being configured to operate said MR scanner to repeat acquiring said volume flow data record with said gradient coil arrangement being operated to encode said MR signals originating from said flow in a plurality of different flow encoding directions;

said processor being configured to, after repeating acquiring said volume flow data record, to reconstruct phase images from said volume flow data record, each phase image being respectively associated with a different flow encoding direction;

said processor being configured to reconstruct magnitude images from said volume flow data record, each of said magnitude images being respectively associated with a respective flow encoding direction;

said processor being configured to calculate deformation fields from said magnitude images;

said processor being configured to apply the calculated deformation fields to the reconstructed phase images, thereby obtaining a plurality of corrected phase images;

said processor being configured to calculate a 4D flow velocity field by executing a phase difference reconstruction algorithm using the corrected phase images; and said processor being configured to make the calculated 4D flow velocity field available in electronic form at an output of said processor.

14. A non-transitory, computer-readable data storage medium encoded with programming instructions, said storage medium being loaded into a control computer of a magnetic resonance (MR) apparatus that comprises an MR scanner having a gradient coil arrangement, said programming instructions causing said control computer to:

operate said MR scanner to acquire a volume flow data record representing flow of a flowing medium in an examination subject situated in the MR scanner, including operating said gradient coil arrangement of the MR scanner to encode MR signals originating from said flow in a single flow encoding direction;

operate said MR scanner to repeat acquiring said volume flow data record, with said gradient coil arrangement being operated to encode said MR signals originating from said flow in a plurality of different flow encoding directions;

after repeating acquiring said volume flow data record, reconstruct phase images from said volume flow data record, each phase image being respectively associated with a different flow encoding direction;

reconstruct magnitude images from said volume flow data record, each of said magnitude images being respectively associated with a respective flow encoding direction;

calculate deformation fields from said magnitude images;

apply the calculated deformation fields to the reconstructed phase images, thereby obtaining a plurality of corrected phase images;

calculate a 4D flow velocity field by executing a phase difference reconstruction algorithm using the corrected phase images; and make the calculated 4D flow velocity field available in electronic form at an output of said control computer.

* * * * *